United States Patent [19]

Dennis et al.

[11] Patent Number: 4,512,973

[45] Date of Patent: Apr. 23, 1985

[54] METHOD FOR OVERCOMING TRYPSIN INHIBITION

[75] Inventors: Mark S. Dennis, San Bruno; David A. Estell, Mountain View; David R. Light, San Francisco, all of Calif.

[73] Assignee: Genentech, Inc., San Francisco, Calif.

[21] Appl. No.: 541,208

[22] Filed: Oct. 12, 1983

[51] Int. Cl.³ .......................... A61K 37/48; A23L 1/20
[52] U.S. Cl. ...................................... 424/94; 426/44; 426/46; 426/52; 426/53; 426/63
[58] Field of Search ...................... 424/94; 426/44, 46, 426/52, 53, 63

[56] References Cited

U.S. PATENT DOCUMENTS

| 3,753,728 | 8/1973 | Bedenk et al. | 426/44 |
| 4,244,973 | 1/1981 | Megen | 426/52 |
| 4,376,128 | 3/1983 | Lunde | 426/46 |

OTHER PUBLICATIONS

Estell et al., Biochemistry, vol. 19, (1980), pp. 124, 125, 129, 130 & 131.
Rackis–Chem. Abst., vol. 83, (1975), p. 54306m.

*Primary Examiner*—Sam Rosen

[57] ABSTRACT

The invention is directed to treating soy based foods with an effective amount of starfish trypsin 1 ($DIT_1$) to inactivate soybean trypsin inhibitor (STI). Also contemplated are the oral administration of starfish trypsin 1 to overcome soybean trypsin inhibitor and pharmaceutical compositions containing starfish trypsin 1.

25 Claims, No Drawings

4,512,973

METHOD FOR OVERCOMING TRYPSIN INHIBITION

BACKGROUND

The field of the present invention is that of food supplements which are commonly prepared from soybeans or soybean meal. The factors of the nutritive qualities of such foodstuffs and their cost of preparation are significant in determining their commercial success and therefore commercial availability. Specifically, the invention concerns methods for improving the quality and the cost efficiency of preparation of foodstuff supplements by overcoming the problem of trypsin inhibition due to a protein native to the soybean preparation.

Trypsin is an important digestive enzyme, particularly in certain species where ancillary enzymes, such as pepsin and chymotrypsin are present in relatively small amounts, or are absent. From an economic standpoint, the most important of these species are chickens, pigs, and calves (when the calves are sufficiently young that they have not developed a fully mature digestive system). In such animals, in particular, if the enzyme trypsin is in some way impaired in its functioning, there are a number of deleterious results. First, any food which is ingested by the animal is lowered in nutritive value because of a directly impaired capacity to digest it. Second, even in animals which contain other digestive enzymes in addition to trypsin, trypsin normally activates some of these enzymes and allows their participation in the process. A deficiency in trypsin thus results in a concomitant deficiency in these enzymes. Finally, in response to a perceived lack of adequate trypsin, the pancreas is induced to release more trypsin than it is capable easily of releasing, resulting in an "overwork" condition called pancreatic hypertrophy, which, at best, results in morbidity and, at worst, in death.

Trypsin inhibition is an insurmountable problem when the ingested foodstuff contains large quantities of soybean materials which have not been subjected to proper treatment to destroy a soybean trypsin inhibitor (STI) which inhibitor is capable of binding the endogenous trypsin in the animal ingesting the foodstuff, and in preventing it from carrying out its normal function. Hence, animal foods which are largely soybean based are currently treated by "cooking" to inactivate this protein. In conventional soy processing, the soybeans are dehulled using a wet process, wherein the water content, however, is purposely limited in order to reduce waste weight and in order to prevent interference with subsequent processing steps. The hulled soybeans are then extracted with hexane to remove the soybean oil for commercial use. After the hexane extraction, the soybean mulch is heated to inactivate the soybean trypsin inhibitor.

This inactivation process is conducted at considerable expense, and with imperfect results. As would be expected, the heating produces a decline in STI content which exponentially decays to a curve assymptotically approaching zero. Therefore, after a time period which is optimum for the particular preparation in question, further heating becomes uneconomic and counterproductive even though additional amounts of STI would be thereby inactivated. The resulting processed soybean meal is then used in animal feeds in a variety of forms, and is reduced in STI but still contains residual amounts.

The most common use of this preparation is as a feed additive which is added to other carbohydrate sources used for livestock feeding, the most important livestock types being pigs and chickens, as well as newborn calves. However, as fed to calves, the preparation is more commonly used as a milk replacement by suspending the preparation in a liquid before feeding. This is formulated either as a solid which may subsequently be made up in liquid form by the livestock raiser, or as a liquid concentrate which is diluted before feeding. Although the constituency is smaller in number, soybean preparations are also used as feeding supplements for human infants, particularly those who exhibit an intolerance for milk products.

The problem of trypsin inhibition has also been studied from a purely research viewpoint. It is known that STI reacts with bovine trypsin by specifically binding to the reactive site of the trypsin; the STI itself being hydrolyzed at the interface due to the action of the inhibited trypsin itself. (Laskowski and Sealock, *Enzymes*, 3rd edition, 375 (1971); Finkenstadt et al., *Proceedings of the International Conference of Proteinase Inhibitors, Second*, 389 (1974). The mechanism of this inhibition is reasonably well understood. Mattis and Laskowski, *Biochemistry* 12: 2239 (1973); Ruhlmann et al., *Journal of Molecular Biology*, 77: 417 (1973); Huber et al., *Journal of Molecular Biology*, 89: 73 (1974), and Sweet et al., *Biochemistry* 13: 4212 (1974). It appears that a fairly tight complex is formed between the inhibitor and the trypsin.

Incubation of catalytic amounts of trypsin with STI results in specific hydrolysis of a single peptide bond, the reactive site. This hydrolysis leads to the establishment of an equilibrium between virgin (reactive site peptide bond intact) and modified (reactive site peptide bond hydrolyzed) inhibitor. Both virgin and modified STI are inhibitors of trypsin, so this hydrolysis will not by itself inactivate STI. Once the modified inhibitor is formed, however, it can be inactivated by further reaction with carboxypeptidase B. This enzyme removes an amino acid (arginine 163) from modified STI. The product of this reaction (des-Arg STI) is no longer capable of inhibiting trypsin. Although trypsin can catalyze the conversion of virgin to modified STI, it does so at such a slow rate (several days at neutral pH) that trypsin cannot be used effectively to inactivate STI.

It has recently been shown, using purified STI, that a starfish, *Dermasterias imbricata*, contains a trypsin enzyme ($DIT_1$) which is capable of converting virgin to modified STI at an extremely rapid rate (several minutes at neutral pH (Estell and Laskowski, *Biochemistry* 19: 124, 1980)). Thus, STI activity can be permanently destroyed by use of this enzyme in combination with another supplementary proteolytic enzyme, for example, carboxypeptidase B, which inactivates the modified STI.

The present invention, therefore, in providing $DIT_1$, offers a solution to the problem of detraction due to the presence of soybean trypsin inhibitor (STI) from desirability of use of soybean as a food.

SUMMARY OF THE INVENTION

The present invention concerns a method for overcoming trypsin inhibition by soybean trypsin inhibitor (STI) in soy based foodstuffs. In the method of the invention, the foodstuff either during its processing, or subsequently, is treated with an effective amount of starfish trypsin-1 (DIT$_1$) and with an effective amount of supplementary proteolytic enzyme.

In another aspect of the invention, a subject animal is fed a formulation of DIT$_1$ and, optionally, supplementary proteolytic enzyme, in a suitable composition, encapsulated so as to protect it from digestion in the stomach, but to permit release in the upper small intestine so as to interact with STI as it progresses through the digestive tract along with the ingested food. (In the case of suitable animals, which normally provide carboxypeptidase B as a digestive enzyme, DIT$_1$ alone, can be administered. The invention is directed to the methods and to compositions suitable for this purpose.)

The use of DIT$_1$ (along with, if necessary, a proteolytic enzyme suitable to remove the free modified STI product from the equilibrium between free modified STI and that bound to trypsin as a complex) is more economical and more efficient than the use of heat deactivation of STI. It is also advantageous in that there are no known reactions which are detrimental as side effects, such as the diminution in vitamin or labile nutrient content which is associated with the heat treatment of the soy preparation.

Accordingly, it is one object of the present invention to provide a simple, effective, and inexpensive way to eliminate the problem of STI inhibition in soybean based foodstuffs.

It is another object of the invention to provide an animal with protection against injested soybean trypsin inhibitor by furnishing the means of inhibitor inactivation directly to the subject animal.

DETAILED DESCRIPTION

A. Definitions

As used herein, "soybean trypsin inhibitor (STI)" is a peptide found in soybeans which is known to bind to trypsin at its active site and to inhibit its proteolytic activity. "Clipped STI" is defined below.

"Starfish trypsin-1" (DIT$_1$) refers to trypsin preparations which are capable of hydrolyzing the trypsin inhibition site in STI and releasing the hydrolyzed STI relatively rapidly. Specifically, the inhibition site comprises the three amino acid sequence tyrosine, arginine, and isoleucine, as amino acid numbers 62, 63, and 64 respectively of the STI chain. DIT$_1$ is proteolytic between the arginine and isoleucine moities, cleaving the STI at this position, to give "clipped STI" or modified STI. The clipped STI remains bound to the trypsin, but is in equilibrium with unbound form.

As used herein, "starfish trypsin-1" or "DIT$_1$" refers to trypsin from the traditional source, namely the starfish, *Dermasterias imbricata*, but is not limited to that particular source. Rather, it refers to trypsin from any source, such as other species of starfish, or any other source which results in an enzyme with these desired properties.

"DIT$_1$-STI complex" refers to the association of DIT$_1$ and STI whether STI is or is not "clipped."

"Supplementary proleolytic enzyme" refers to any enzyme which, by virtue of its ability to further hydrolyze STI clipped by DIT$_1$ serves to shift the equilibrium between bound and unbound clipped STI by removing the unbound clipped STI. Carboxypeptidase B is one such supplementary proteolytic enzyme. It is commercially available, and is specific for cleaving the linkage between arginine and isoleucine remaining in the clipped STI. Any other proteases capable of cleaving this linkage specifically will be satisfactory for the process of the invention, as well as proteases which cleave other appropriately placed peptide bonds in STI.

"Soy based foodstuffs" include any foodstuff intended for human or animal consumption which contains substantial amounts of soybean meal or other soybean derived substances as part of it. Common among these foodstuffs are livestock feed and feed supplements which are prepared by simply grinding or chopping soybean meal which has been extracted for soybean oil (or which has not), liquid emulsions which are intended as milk supplements for calves, baby food formulae which are intended for infants who are allergic to the proteins in milk, and a number of other preparations less commonly encountered.

"Soybean meal" refers to extracted or unextracted soybean material which is sufficiently processed mechanically or otherwise to expose the contained soybean trypsin inhibitor to chemical or enzymatic reagents. "Dry weight" of soybean meal refers to the weight of the meal alone, *including* its autochthonous moisture, but excluding any emulsifying or processing solvent.

B. Enzyme Preparations

The enzyme DIT$_1$ has been, and can be, isolated from a source known to contain it, most commonly the starfish, *Dermasterias imbricata*, according to the method of Estell and Laskowski (supra) incorporated herein by reference. However, the method and composition of the invention includes the use of this enzyme derived by any mode of preparation, including recombinant DNA techniques. The enzyme herein is defined by its ability to cleave, and release under suitable conditions, soybean trypsin inhibitor. All enzymes with this property are included in the method of this invention, regardless of their source.

Carboxypeptidase B is available commercially from a number of suppliers such as, for example, Sigma, Inc. This enzyme is suitable for the invention however prepared. As stated above, other suitable supplementary proteolytic enzymes are applicable to the method and composition of the invention, so long as they catalyze cleavage of amino acid linkages in STI which result in its being released from the DIT$_1$-STI complex in a form which is incapable of reforming the complex.

C. Method of Treating Soy Based Foodstuffs

In that aspect of the invention which relates to a method for treating soy based foodstuffs, the soy trypsin inhibitor is brought into contact with the DIT$_1$ and supplementary proteolytic enzyme directly in an in vitro reaction mixture. In order for the DIT$_1$ and supplementary proteolytic enzyme to function, the STI contained in the soybeans must be exposed for direct chemical contact with these enzymes, and a minimum amount of water must be present so as to provide a suitable medium for reactivity. If dry soybeans are used, the STI exposed by breaking the soybeans open, and optionally, further mechanical processing, sufficient water or other aqueous medium must be added so as to effect efficient contact between the enzymes and their intended substrate. It appears that a minimum of approximately 10 percent water of the dry weight of soybean is required to effect this consequence. (As noted above, "dry weight" of soybean or meal refers to the weight of the soybeans without any added moisture or solvent. However, it includes the water normally present in the soybeans.)

As soybeans are often processed, the soybean meal is prepared by dehulling the beans and then extracting using hexane in order to prepare soybean oil. This process can be modified by using isopropanol in the extraction procedure, thus providing a more polar medium which may necessitate less added water than would be otherwise necessary. Thus, in the context of the present invention, it may be possible to reduce the amount of added water when this prior extraction with isopropanol takes place.

In many applications of the present invention, the soybean meal is to be used as a liquid suspension when supplied to the subject animal. In this case, the amount of water present in the preparation is clearly sufficient to mediate the enzyme activity.

Thus, in carrying out the process of the invention, a soybean meal preparation which contains sufficient water to effectively expose the soybean trypsin inhibitor to the action of the enzymes described is used. To this preparation is added a proteolytically effective amount of $DIT_1$, which amount is in the range of between 1 and 100 mg $DIT_1$ per 100 grams of soybean meal "dry weight". A preferred range is between about 5 mg to 20 mg of $DIT_1$ per 100 grams soybean meal. If carboxypeptidase B is used as a supplementary proteolytic enzyme, effective proteolytic amounts are in the same range based on 100 grams of soybean meal as those given for $DIT_1$; the preferred range for carboxypeptidase B is slightly higher from about 10 mg to about 50 mg per 100 grams of soybean meal. Other supplementary proteolytic enzymes may also be used, but of course, the effective and preferred amounts will vary according to the specific activity of the particular choice. The mixture is then incubated from approximately 15 minutes to 12 hours, preferably around 3–4 hours at about 10° C. to 40° C., preferably around 25° C. The pH should be maintained in the range of approximately 6 to 10, preferably close to 8.2. If other choices besides carboxypeptidase B are made for the supplementary enzyme, slight variations in this pH range may be preferred. The pH may be adjusted by addition of suitable buffering materials, such as preferably, Tris.

The preparation which has been thus processed can then be used normally in the foodstuff, as the added $DIT_1$ and supplementary enzyme do not confer any deleterious effects on the preparation nor do they constitute a health hazard to the animal ingesting the preparation.

D. In Vivo Process of the Invention

An alternative aspect of the present invention relates the use of the system herein described in vivo to inactivate the STI as it goes through the digestive tract of a subject animal and to suitable compositions to be employed in this method.

Suitable subject animals include human beings, usually human infants which are administered soybean preparations as food supplements. There is, of course, no reason that this would be inappropriate to adults, except that unless a human adult relies on untreated soybeans as an important food source, sufficient alternative digestive methods are available. Of greater economic consequence at the present is the use of this aspect of the invention in domestic livestock which relies on soybeans as a food source. As pointed out above, especially those forms of livestock which are dependent on trypsin as the major digestive enzyme, such as pigs, chickens, and young calves are suitable subjects. There is, of course, no theoretical reason why the invention could not relate to the enhancement of the diet of any domestic or wild bird.

In this aspect of the invention, the $DIT_1$ preparation or a composition containing it is administered to the subject animal directly. If the animal has a supplementary proteolytic enzyme available in its own digestive tract, as many do, it is unnecessary to include this enzyme in the preparation. For example, human infants and baby calves have in their digestive tracts sufficient quantities of carboxypeptidase B to make the $DIT_1$ preparation effective when administered alone. If the subject animal does not have this capability, the supplementary enzyme, preferably carboxypeptidase B, must be added to the composition.

It will be clear, that a formulation or composition containing the $DIT_1$ and, optionally, the supplementary proteolytic enzyme, must be prepared in such a fashion that the active ingredients traverse the stomach and substantial amounts enter the small intestine. That is, of course, the location at which the trypsin secreted by the pancreas enters the digestive tract. Accordingly, the enzymes must be packaged in a suitable coating which is impervious to acid but labile in base, or, alternatively, formulated in such a slowly dissolving form that an effective amount remains when the preparation enters the small intestine.

Methods of preparing such dosage forms are known, or will be apparent, to those skilled in the art of pharmaceutical formulations; for example, see *Remington's Pharmaceutical Sciences*, Mack Publishing Company, Easton, Penna., 15 ed., 1975. In any event, the composition or formulation to be administered will contain a quantity of the active compound(s) in an amount effective to accomplish the purpose herein stated, along with acceptable pharmaceutical excipients.

For oral administration, normally employed excipients include, for example, pharmaceutical grades of mannitol, lactose, magnesium stearate, sodium saccharin, talcum, cellulose, magnesium carbonate, and the like. Such compositions take the form of, in this case, tablets, pills, or preferably capsules, which have the aforementioned capability to transcend the stomach relatively unaffected. Such compositions may contain approximately 5–95 percent of the active ingredient (or ingredients if the supplementary enzyme is added) preferably 25–70 percent.

Although clearly not preferred, it may be possible to administer this composition parenterally in particular instances. The active ingredient must be present in the small intestine when the soybean meal goes through the digestive tract.

With regard to timing, the composition should be administered to effect the foregoing results. It appears that for most practical applications, the animals should ingest the composition within about 4 hours prior to ingesting the foodstuff which contains the soybean meal. The timing may vary according to the formulation of the composition of course, and according to the rigor of the conditions which are found in the digestive tract of the subject animal. However, four hours before feeding appears to be a reasonable estimate for most cases.

The amount of the composition to be administered is, of course, determined by the quantity of STI which is present in the soybean meal to be fed, as well as on the percentage of active ingredients in the composition. Based on the amount active ingredient $DIT_1$, suitable amounts are in the range of $10^{-5}$ to $10^{-2}$ g $DIT_1$ to one gram of dry weight of soybean meal fed. (It is assumed that the quantity of foodstuff supplied is designed so as to equal the amount of foodstuffs actually ingested. Experienced keepers of livestock are capable of making these estimates with considerable certainty. While this may be less so in the case of human subjects, suitable adjustments can be made for lack of appetite, etc.) Preferable amounts to be administered are in the range of approximately 5 mg to 100 mg of $DIT_1$ to 100 grams of soybean meal fed.

The amount of supplementary proteolytic enzyme administered will, of course, depend on the capacity of the individual animal to supply its own such enzyme, and upon the nature of the supplementary enzyme used. If carboxypepidase B is to be used as the supplementary enzyme and is added externally, the quantities required and preferred are approximately the same as those required for $DIT_1$.

E. Examples

The following examples are intented to illustrate the invention but should not be construed as limiting it.

Example 1

Inactivation of STI in Soybean Meal

A suspension of soybean of meal was prepared as follows: Approximately 5 grams of dry soybeans were treated for 5 minutes at high speed in a Waring blender to obtain dry meal. For each sample, 25 mg of the dry meal was suspended in a reaction mixture whose total volume was 225 $\mu l$, and which contained 25 $\mu g$ $DIT_1$, 80 $\mu g$ carboxypepidase B, and was 0.05M Tris, pH 8.2. The reaction mixture was incubated at 25° C. 20 $\mu l$ samples were withdrawn at times 0, 4, and 17.5 hours, brought to 1.5 molar HCl for 25 minutes to destroy $DIT_1$ activity, diluted to neutral pH in a final volume of 2 ml, and then assayed for STI as follows:

Samples of 3, 6, and 9 $\mu l$ were removed and added respectively to 1 ml reaction mixtures containing 0.05M Tris, pH 8.2, 0.02 molar $CaCl_2$, 10 $\mu l$ trypsin solution containing 833 picomoles of trypsin and 10 $\mu l$ of a DMSO solution containing 43.5 mg per ml of BAPA, a trypsin substrate. The trypsin activity inhibition was accessed by monitoring the trypsin activity at 410 nanometers according to the method of Erlanger et. al., *Arch. Biochem. Biophys.*, 95: 271 (1961), incorporated herein by reference. It was found that after four hours of incubation, 85 percent of the STI activity was removed; after 17.5 hours, 93 percent of the inhibitory activity originally present had disappeared. The 7 percent residual trypsin inhibition is most likely due to competitive inhibition by other proteins rather than remaining active STI as is shown by the gel assay technique of Example 2 (below). A control sample using 1.5 $\mu g$ of purified STI in place of the 25 mg of soybean meal was run concomitantly and indicated 100 percent destruction of the inhibitory activity after four hours.

It was demonstrated that trypsin activity in the above assay for STI arises from the trypsin in the assay and not from residual $DIT_1$ which is not inactivated by treatment with HCl as follows: Measurement of residual $DIT_1$ activity in the treated soybean meal supernatant demonstrated that between 98.5 percent and 99.5 percent is destroyed by the HCl treatment and that the residual activity accounts for a maximum of 1 percent of the trypsin activity in the assay. In addition, HCl treatment of soybean meal (untreated with $DIT_1$) under the conditions used to inactivate added $DIT_1$ was shown to have no effect on the STI content.

Example 2

Distribution of Clipped STI in Supplementarily Cleaved and Uncleaved Forms

A preparation containing 25 mg ground soybean meal was prepared as in Example 1 and incubated in a total volume of 260 $\mu l$ containing 10 $\mu g$ carboxypepidase B and 0.5 molar Tris, pH 8.2, at 25° C. Two identical soybean samples were run, one containing 1.25 $\mu g$ $DIT_1$, the other twice that quantity. Samples were removed periodically and assayed by gel electrophoresis according to the method of Luthy et al., *J. Biol. Chem.*, 248: 1760 (1973), incorporated herein by reference, to assess the status of STI. As this procedure separates on the basis of charge, the presence of intact STI (I), clipped (I*), and clipped and supplementarily cleaved STI (I*C), can be assessed. Table 1 shows the results of this assay. It is clear from these results that the initially clipped STI (I*) progressively migrates into the I*C form.

TABLE 1

| | 1.25 ug $DIT_1$ | | | 2.5 ug $DIT_1$ | | |
|---|---|---|---|---|---|---|
| Time (hr) | I (percent) | I* (percent) | I*C (percent) | I (percent) | I* (percent) | I*C (percent) |
| 0 | 100 | 0 | 0 | 100 | 0 | 0 |
| 1 | 70 | 4 | 26 | 41 | 28 | 31 |
| 2 | 32 | 11 | 57 | 11 | 15 | 74 |
| 3 | 17 | 5 | 78 | 7 | 3 | 90 |
| 5 | 5 | 0 | 95 | 0 | 1 | 99 |
| 9 | 5 | 0 | 95 | — | — | — |
| 24 | 0 | 0 | 100 | — | — | — |

Example 3

Effect of Carboxypepidase B Activity on Inactivation

In a procedure similar to that setforth in Example 1, the amount of STI activity removed after a period of 4 hours was assayed as a function of carboxypepidase B amount present in the reaction mixture, by assessing trypsin activity according to the method of Erlanger. In addition, STI, I*, and I*C amounts were assayed by gel electrophoresis. Each sample contained 25 mg ground soybeans, 3.13 $\mu g$ $DIT_1$, in 0.05 molar Tris pH 8.2 in a total volume of 260 $\mu l$. Incubations were done at 25° C. The results are shown in Table 2.

TABLE 2

| | Gel Assay | | | Enzyme Activity Assay Removed |
|---|---|---|---|---|
| Carboxypeptidase B ($\mu l$) | I (percent) | I* (percent) | I*C (percent) | |
| 0.2 | 30 | 48 | 32 | 29 |
| 2 | 14 | 22 | 63 | 39 |
| 20 | 0 | 0 | 100 | 62 |

As the results show, carboxypepidase B or other supplementary proteolytic enzyme must be present to effect any inhibition removal activity. As the carboxypeptidase B is required for timely dissociation of the STI-$DIT_1$ complex, $DIT_1$ alone cannot be effective in STI removal.

We claim:

1. A method for overcoming trypsin inhibition by soybean trypsin inhibitor (STI) in soy based foodstuffs, which method comprises treating the soybean meal used in said foodstuff with a proteolytically effective amount of starfish trypsin 1 ($DIT_1$) and with a proteolytically effective amount of supplementary proteolytic enzyme.

2. The method of claim 1 wherein the supplementary proteolytic enzyme is carboxypeptidase B.

3. The method of claim 1 wherein the soy based foodstuff is an aqueous soybean meal suspension.

4. The method of claim 1 wherein the soy based foodstuff is a preparation of soybean meal processed for livestock feed.

5. The method of claim 1 wherein the soybean meal contains at least 10 percent added water.

6. The method of claim 1 wherein the dry weight ratio of $DIT_1$ to soybean meal is between $10^{-5}$ and $10^{-3}$.

7. The method of claim 2 wherein the dry weight ratio of carboxypeptidase B to soybean meal is between $10^{-5}$ and $10^{-3}$.

8. The method of claim 6 wherein the dry weight ratio of carboxypeptidase B to soybean meal is between $10^{-5}$ and $10^{-3}$.

9. A method of overcoming trypsin inhibition by soybean trypsin inhibitor in a subject animal, which method comprises administering orally to said animal a proteolytically effective amount of, or a composition containing an proteolytically effective amount of, $DIT_1$ in a dosage form resistant to the digestive conditions of the stomach.

10. The method of claim 9 wherein the composition also includes a proteolytically effective amount of a supplementary proteolytic enzyme.

11. The method of claim 10 wherein the supplementary proteolytic enzyme is carboxypeptidase B.

12. The method of claim 9 wherein the $DIT_1$ or $DIT_1$ composition is administered within about 4 hours prior to ingestion by the animal of soybean meal containing foodstuff.

13. The method of claim 10 wherein the $DIT_1$ or $DIT_1$ composition is administered within about 4 hours prior to ingestion by the animal of soybean meal containing foodstuff.

14. The method of claim 11 wherein the $DIT_1$ or $DIT_1$ composition is administered within about 4 hours prior to ingestion by the animal of soybean meal containing foodstuff.

15. The method of claim 12 wherein the $DIT_1$ administered is in the dry weight ratio of between about $10^{-5}$ and $10^{-2}$ to the soybean meal containing foodstuff ingested.

16. The method of claim 13 wherein the $DIT_1$ administered is in the dry weight ratio of between about $10^{-5}$ and $10^{-2}$ to the soybean meal containing foodstuff ingested.

17. The method of claim 14 wherein the $DIT_1$ administered is in the dry weight ratio of between about $10^{-5}$ and $10^{-2}$ to the soybean meal containing foodstuff ingested.

18. The method of claim 14 wherein the carboxypeptidase B administered is in the dry weight ratio of between about $10^{-5}$ and $10^{-2}$ to the soybean meal containing foodstuff ingested.

19. The method of claim 17 wherein the carboxypeptidase B administered is in the dry weight ratio of between about $10^{-5}$ and $10^{-2}$ to the soybean meal containing foodstuff ingested.

20. A composition suitable for confering the ability to inactivate STI in the intestinal tract of a subject animal, which composition comprises a proteolytically effective amount of $DIT_1$ in admixture with a pharmaceutically acceptable excipient.

21. The composition of claim 20 which also includes a proteolytically effective amount of supplementary proteolytic enzyme.

22. The composition of claim 21 wherein the supplementary proteolytic enzyme in carboxypeptidase B.

23. The composition of claim 20 wherein the amount of $DIT_1$ is between about 5 percent and 95 percent by weight of the composition.

24. The composition of claim 22 wherein the sum of the amounts of $DIT_1$ and carboxypeptidase B is between about 5 percent and 95 percent by weight of the composition.

25. A composition comprising soybean meal and a proteolytically effective amount of $DIT_1$, said soybean meal containing STI which has been substantially inactivated by proteolysis in the presence of the $DIT_1$.

* * * * *